US006804991B2

United States Patent
Balschat et al.

(10) Patent No.: US 6,804,991 B2
(45) Date of Patent: Oct. 19, 2004

(54) METHOD AND DEVICE FOR DETECTING A LEAKAGE IN A FLUID SYSTEM OF A BLOOD TREATMENT APPARATUS

(75) Inventors: Klaus Balschat, Schwebheim (DE); Helmuth Ender, Zeil am Main (DE); Alfred Gagel, Litzendorf (DE); Reiner Spickermann, Wasserlosen-Burghausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 116 days.

(21) Appl. No.: 10/342,851

(22) Filed: Jan. 14, 2003

(65) Prior Publication Data

US 2003/0136181 A1 Jul. 24, 2003

(30) Foreign Application Priority Data

Jan. 15, 2002 (DE) ........................................ 102 01 109

(51) Int. Cl.[7] .......................... G01M 3/04; B01D 35/14
(52) U.S. Cl. ....................... 73/40.5 R; 73/1.35; 210/90; 210/646; 604/4.01
(58) Field of Search ............................ 73/40.5 R, 1.35; 210/90, 644–646; 604/4.01

(56) References Cited

U.S. PATENT DOCUMENTS

| 3,893,332 | A | * | 7/1975 | Dolan et al. ................... 73/40 |
| 4,148,314 | A | * | 4/1979 | Yin .............................. 210/90 |
| 4,608,857 | A | * | 9/1986 | Mertens et al. .......... 73/40.5 R |
| 5,431,811 | A | | 7/1995 | Tusini et al. |
| 5,580,460 | A | * | 12/1996 | Polaschegg ................. 210/646 |
| 6,530,262 | B1 | * | 3/2003 | Esser ....................... 73/40.5 R |
| 6,572,576 | B2 | * | 6/2003 | Brugger et al. ............... 210/90 |

FOREIGN PATENT DOCUMENTS

DE          42 39 937 A1     1/1994

* cited by examiner

Primary Examiner—Michael Cygan
(74) Attorney, Agent, or Firm—Kenyon & Kenyon (57) ABSTRACT

In order to detect a leakage in a fluid system of a blood treatment apparatus having an extracorporeal blood circuit, the pressure in the fluid system is measured continuously during a predetermined period of the duration of treatment, and the leak rates are calculated from the change in the pressure at predetermined time intervals of the predetermined period of the duration of treatment. The leakage volume in the predetermined period of the duration of treatment is calculated from the leak rates, and the leakage volume is compared with a predetermined limit value. If the leakage volume is greater than the limit value, this indicates a possible loss of leaktightness in the system. This can be verified with a conventional pressure-holding test. The method and device are characterized by the fact that it is not necessary in principle to interrupt the blood treatment in order to detect a loss of leaktightness.

20 Claims, 4 Drawing Sheets

METHOD AND DEVICE FOR DETECTING A LEAKAGE IN A FLUID SYSTEM OF A BLOOD TREATMENT APPARATUS

FIELD OF THE INVENTION

The invention relates to a method and a device for detecting a leakage in a fluid system of a blood treatment apparatus having an extracorporeal blood circuit, in particular a blood treatment apparatus having a dialyzer which is divided by a semipermeable membrane into a blood chamber and a dialysis fluid chamber.

BACKGROUND OF THE INVENTION

Hemodialysis apparatuses with an ultrafiltration (UF) control means are now in widespread use. The UF control means allow a defined ultrafiltration quantity to be preset. It is known that a defect can cause a UF control means to lose its ability to exactly control the ultrafiltration rate. Since an ultrafiltration rate which is drastically increased or decreased by such a defect can endanger the patient's life, known safety standards demand that a protection system be present in order to prevent an ultrafiltration which poses a danger to the patient. Monitoring of the transmembrane pressure (TMP) is accepted as one such protection system.

In practice, the balance error upon ultrafiltration can amount to at most 500 ml during a treatment session. In the case of a treatment session which lasts 4 hours, this corresponds to a mean volume flow of only 125 ml/h.

However, the development of dialyzers having high-permeability membranes, known as high-flux dialyzers, has led to a situation where monitoring of the TMP cannot detect a dangerously high or low ultrafiltration rate with sufficient resolution, as a consequence of the limited resolution of the TMP sensor.

In order to at least ensure that the treatment begins with an intact UF control system, there are commercially available means which permit a manual or automatic check of the integrity of the control system prior to treatment. This check is done by carrying out a pressure-holding test in the dialysis part of the equipment.

German Patent Application No. 42 39 937 A1 describes a method and a device for detecting a leakage in the fluid system of a hemodialysis apparatus on the basis of a pressure-holding test with which the functionality of the control system for the ultrafiltration rate can also be checked during the dialysis treatment. To carry out the pressure-holding test, the dialyzer is separated from the dialysis fluid part of the hemodialysis apparatus at periodic intervals during the dialysis, and in each case for a short time interval, and the pressure course in the dialysis fluid outside the separated dialyzer is recorded for any deviation from the stable state in the sense of a pressure-holding test. This method has proven useful in practice but has the disadvantage that the dialysis treatment has to be interrupted at regular intervals for the pressure-holding test. A further disadvantage is that a leak cannot be quantitatively recorded.

SUMMARY OF THE INVENTION

It is an object of the invention to make available a method by which it is possible in principle to detect leakages in the fluid system of a blood treatment apparatus without interrupting the blood treatment. It is also an object of the invention to make available a device which permits detection of leakages without interrupting the treatment.

The method according to the invention is based on a continuous measurement of the pressure in the fluid system of the blood treatment apparatus during a predetermined period of the duration of treatment, where this period can be a part of the duration of treatment or even the entire duration of treatment.

It has been found that above all the change in the static pressure in the fluid system of the blood treatment apparatus provides an indication of the presence of a leakage. The pressure can in principle be measured at any point of the fluid system. In a hemodialysis apparatus with a dialyzer which is divided by a semipermeable membrane into a blood chamber and a dialysis fluid chamber, it is possible to measure the pressure in the dialysis fluid line upstream and/or downstream of the dialysis fluid chamber of the dialyzer. It is also possible to carry out measurements in the blood line upstream and/or downstream of the blood chamber. The crucial factor is that the change in the pressure is continuously recorded during the blood treatment.

From the change in the pressure, the leak rates are calculated during the blood treatment at predetermined time intervals of the predetermined period of the duration of treatment. The leakage volume in the predetermined period of the duration of treatment is then calculated from the leak rates. The calculation of the leakage volume is thus effected by means of integration of the continuously calculated leak rates. In this way, the overall leakage amount is quantitatively available at all times. The leakage volume is then compared with a limit value. If the limit value is exceeded, this points to a possible malfunction.

To calculate the change in the pressure during the predetermined period, a pressure value is preferably continuously calculated in succeeding cycles and compared with a pressure reference value. If a leak suddenly occurs, the pressure signals change very quickly in a typical range of a few seconds to one minute. Leakages are reliably detected if the delay time $\Delta t$ between the pressure value and the pressure reference value is likewise a few minutes. The pressure reference value should be the pressure value which was measured in a preceding cycle. In this way, slow pressure changes resulting from parameter drifts can be eliminated. In the case of insidious leaks, by contrast, it is possible that an initially leaktight system has a small leak rate which steadily rises over the course of time. The decisive factor here is not the gradient, but the duration of the change. Insidious leaks can be reliably detected if the pressure reference value is the pressure at the start of the predetermined period, i.e., the pressure reference value is constant.

The pressure value to be determined can be the instantaneously measured pressure in the fluid system. It is advantageous to calculate the pressure value by statistically evaluating a multiplicity of measurements in a predetermined time interval. The pressure value is preferably a mean value of the pressure values measured in an averaging interval. The averaging interval should here have a sufficient length in order to obtain characteristic measurement variables.

The measured pressure signal is generally superposed by various interference signals which are attributable in particular to the operation of the dialysis fluid and blood pump, the operation of the ultrafiltration pump, and the change-over of the balance chambers. A wide variety of methods can be used to eliminate these interference variables. As the interference variables have a characteristic signal course, they can be detected and shut out. The important factor is that the pressure change is calculated using a pressure signal which is as free as possible from interference variables.

If the leakage volume exceeds the predetermined limit value, an alarm can be given which points to a possible malfunction. However, it is also possible that a malfunction will only be assumed to exist when loss of leaktightness in the fluid system is established on the basis of the known pressure-holding test. For this purpose, when the predetermined limit value is exceeded, the blood treatment is interrupted and the pressure-holding test is carried out with the appropriate sensitivity. Thus, interruption of the blood treatment only takes place if there is a high probability of a leakage. If loss of leaktightness is detected by means of the pressure-holding test, an acoustic and/or optical alarm can be given. It is also possible to intervene in the blood treatment, in which case the blood treatment is preferably interrupted.

However, if the pressure-holding test does not reveal any loss of leaktightness, monitoring of the fluid system on the basis of the continuous pressure measurement is preferably reinitiated.

The pressure value can be calculated from the pressure measured at one or more points of the fluid system. Leakages have a particularly strong influence on the mean value between the pressure in the dialysis fluid upstream and downstream of the dialyzer. In addition, the transmembrane pressure can also be used. The pressure can also be measured only on the blood side. Thus, for example, leakages can be detected with only measurement of the pressure of the blood downstream of the blood chamber, which pressure is affected by the pressure drop on the needle, for example, as a result of the blood flowing back to the patient. In the event of a leak, some of the liquid blood stream flows through the membrane to the dialysate side, as a result of which the blood flow is reduced by this amount, so that the pressure in the blood stream downstream of the blood chamber falls.

In principle it is also possible for the monitoring to be carried out using a plurality of pressure values based on different pressure measurements. In this way a plausibility check is possible. For example, a particular indication of a leakage in this case is if the transmembrane pressure rises and the pressure in the blood stream downstream of the blood chamber falls.

It has been found that the ultrafiltration rate and the leak rate are equivalent disturbances in respect to the static pressure. Therefore, the influence of a leakage on the pressure in the fluid system can be simulated prior to treatment, in terms of amount and direction, by varying the UF rate. During treatment, the measurement values can then be compared accordingly.

The device for detecting a leakage has a controlling and computing unit, means for recording the pressure measurement values, means for calculating the leak rates, means for calculating the leakage volume, and means for comparing the leakage volume with a limit value. Such means can be provided by a microprocessor with corresponding software and suitable pressure sensors. Since a microprocessor and pressure sensors are present anyway in the known blood treatment apparatuses, the technical outlay is low.

DETAILED DESCRIPTION

An illustrative embodiment of the invention is explained in more detail below with reference to the drawings.

Figure 1:
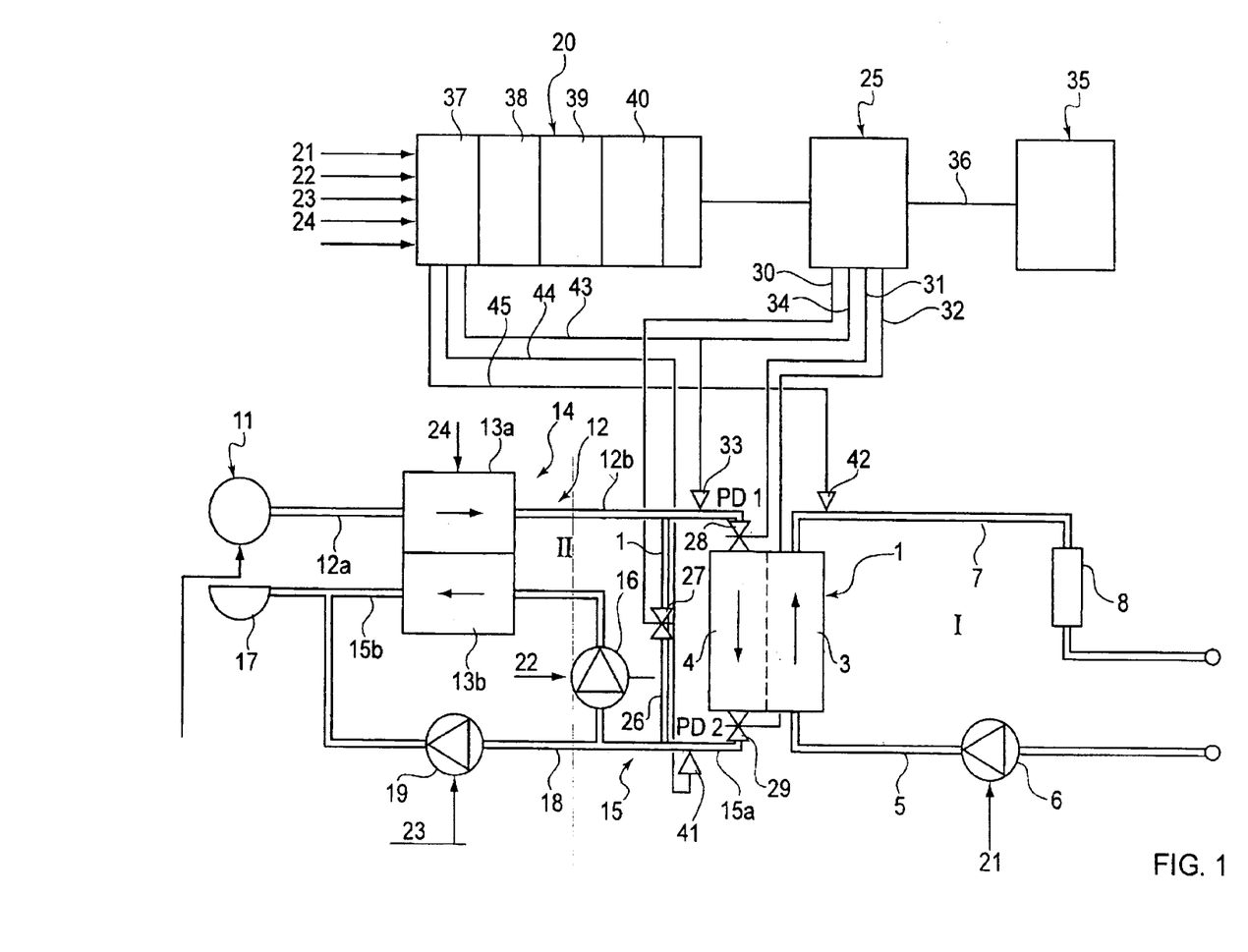
FIG. 1 shows, in a diagrammatic representation, the main components of a hemodialysis apparatus having a device for detecting a leakage.

FIG. 1 is a diagrammatic representation of the main components of a hemodialysis apparatus together with a device for detecting a leakage in the fluid system of the dialysis apparatus.

The hemodialysis apparatus has an extracorporeal blood circuit I and a dialysis fluid system II. The extracorporeal blood circuit I and the dialysis fluid system II form the fluid system of the dialysis apparatus.

The dialysis apparatus has a dialyzer 1 which is divided by a semipermeable membrane 2 into a blood chamber 3 and a dialysis fluid chamber 4. The inlet of the blood chamber is connected to one end of a blood delivery line 5 into which a blood pump 6 is coupled, while the outlet of the blood chamber 3 is connected to one end of a blood discharge line 7 into which a drip chamber 8 is coupled. This part of the fluid system represents the extracorporeal blood circuit I of the dialysis apparatus.

The dialysis fluid system II of the dialysis apparatus has a means 11 for preparing dialysis fluid. It is connected to the inlet of the first chamber half 13a of a balance means 14 via a first section 12a of a dialysis fluid delivery line 12. The second section 12b of the dialysis fluid delivery line 12 connects the outlet of the first balance chamber half 13a to the inlet of the dialysis fluid chamber 4. The outlet of the dialysis fluid chamber 4 is connected to the inlet of the second balance chamber half 13b of the balance means 14 via the first section 15a of a dialysis fluid discharge line 15. A dialysis fluid pump 16 is coupled into the first section 15a of the dialysis fluid discharge line 15. The outlet of the second balance chamber half 13b is connected to an outflow 17 via the second section 15b of the dialysis fluid discharge line 15. Upstream of the dialysis fluid pump 16, an ultrafiltrate line 18 branches off from the dialysis fluid discharge line 15 and likewise leads to the outflow 17. An ultrafiltration pump 19 is coupled into the ultrafiltrate line 18.

In FIG. 1, for the purposes of improved clarity, only the two chamber halves of the first balance chamber are shown. However, the balance means 14 also has a second balance chamber which is coupled in parallel to the first chamber. In addition, the balance means also has valves (not shown) for controlling the flow of dialysis fluid. Such balance systems are described, for example, in German Patent Application No. 28 38 414 or German Patent No. 197 08 391.

The apparatus shown in FIG. 1 can also be used for hemofiltration by suppressing the flow of dialysis fluid through the dialysis fluid chamber 4 and at the same time ensuring a suitable administration of substitution fluid to the patient. For simplicity, however, the following text will discuss the "dialysis apparatus."

The dialysis apparatus also has a central controlling and computing unit 20 which is connected via control lines 21 to 24 to the blood pump 6, the dialysis fluid pump 16, the ultrafiltration pump 19 and the balance means 14. The controlling and computing unit 20 sends the control commands to the individual components and receives, from the components, data concerning the operational states of the components, for example, the output rates of the pumps, the balance chamber cycles, etc.

During the hemodialysis treatment, the patient's blood flows through the blood chamber 3, and the dialysis fluid runs through the dialysis fluid chamber 4 of the dialyzer 1. Since the balance means 14 is coupled into the dialysis fluid circuit II, the amount of dialysis fluid flowing in via the dialysis fluid delivery line 12 can only be as much as there is dialysis fluid able to flow out via the dialysis fluid discharge line 15. With the ultrafiltration pump 19, fluid can be withdrawn from the patient via the dialyzer 1.

To check the dialysis fluid system I for loss of leaktightness, the dialysis apparatus has a means 25 with which a pressure-holding test can be carried out. For this purpose, the dialysis fluid delivery and discharge lines 12, 15 are connected to a bypass line 26 into which a bypass valve 27 is coupled. Moreover, upstream and downstream of the dialysis fluid chamber 4 of the dialyzer 1, shutoff valves 28, 29 are coupled into the dialysis fluid delivery and discharge lines. The bypass valve 27 and the shutoff valves 28, 29 are electromagnetically activatable valves which are connected via control lines 30, 31, 32 to the means for checking the fluid system 25. A pressure sensor 33 is also provided which measures the pressure in the second section 12b of the dialysis fluid delivery line 12 upstream of the dialysis fluid chamber 4. This pressure sensor is also connected to the means 25 via a data line 34.

The dialysis fluid system is checked for loss of leaktightness after interrupting the dialysis treatment as follows. The means 25 closes the shutoff valves 28, 29 and opens the bypass valve 27 for the duration of the test interval T, so that the dialysis fluid chamber 4 is separated from the dialysis fluid system II. During the test interval T, the means 25 monitors the operating pressure in the dialysis fluid system II with the pressure sensor 33 and compares the operating pressure with a predetermined limit value. During the test interval, the pressure initially rises, levels out and, in the case of an intact system, remains stable. By contrast, if there is a leak, it drops below the predetermined limit value. This pressure drop is a clear indicator that the UF control system is no longer integral. If the operating pressure thus drops below the predetermined limit value, the means 25 generates an alarm signal, which an alarm means 35 receives via a data line 36. The alarm means 35 thereupon gives an acoustic and/or optical alarm. In addition, the whole dialysis treatment can be interrupted. This pressure-holding test for detecting a leakage is described in detail in German Patent Application No. 42 39 937 A1, which is incorporated by reference herein.

In addition to the means 25 for checking the dialysis fluid system by means of a pressure-holding test, the dialysis apparatus has a further device for detecting a leakage in the fluid system. This device has a controlling and computing unit which forms part of the central controlling and computing unit 20 of the dialysis apparatus. However, it is also possible to provide a separate controlling and computing unit. The controlling and computing unit has means 37 for recording the pressure measurement values, means 38 for calculating leak rates, means 39 for calculating a leakage volume, and means 40 for comparing the leakage volume with a predetermined limit value. These means are shown in FIG. 1 as part of the central controlling and computing unit 20.

For measuring the pressure in the fluid system, in addition to the first pressure sensor 33, there is a second pressure sensor 41 which measures the pressure downstream of the dialysis fluid chamber 4 in the first section 15a of the dialysis fluid discharge line 15. A third pressure sensor 42 measures the pressure in the blood discharge line 7 downstream of the blood chamber 3. The pressure sensors 33, 41, 42 are connected to the controlling and computing unit 20 via data lines 43 to 45.

The method according to the invention for detecting leakages is described with reference to the following simplified model for the static pressure in the fluid system.

It is assumed that the dialysis fluid flow $Q_D$ does not change the static pressure in the fluid system. There are only dynamic pressure drops at the flow resistance points, but these are not taken into account when considering the static pressure. The static pressure $P_D$ is the same at all points in the fluid system. The mean pressure $P_B$ of the blood pump 6 is assumed to be constant if the blood volume flow is constant. Since, as will be explained below, the invention takes account of pressure differences, the dynamic pressure drops are not relevant anyway in the case of constant flows.

The compliance of the individual components of the fluid system, which compliance is attributable to the use of hose lines, is combined in an overall compliance C for which:

$$C = \frac{dV_c}{dP_D} = \frac{Q_c}{dP_D/dt} \tag{1.1}$$

where $V_C$=volume stored in the compliance;
$Q_C$=volume flow flowing into the compliance; and
$P_D$=static pressure on the dialysate side.

The pressure drop on the membrane 2 of the dialyzer 1 is described by the following equation:

$$Q_{TM}=K_{UF}*P_{TM} \tag{1.2}$$

where $$P_{TM}=P_B-P_D \tag{1.3}$$

where $P_{TM}$=transmembrane pressure [hpa]
$Q_{TM}$=flow through the membrane [ml/h]
$K_{UF}$=ultrafiltration coefficient.

The volume flow $Q_{TM}$ flows through the membrane from the blood side to the dialysate side into the dialysis fluid circuit II. The volume flows are withdrawn through the ultrafiltration pump 19 ($Q_{UF}$) and possibly through a leak ($Q_L$). The resulting net volume flow flows into the compliance $Q_C$ and thereby generates a change in the static pressure $P_D$. The balance of the individual volume flows gives:

$$Q_{TM}-Q_{UF}-Q_L=Q_C \tag{1.4}$$

Equations (1.1), (1.2) and (1.3) give:

$$C*\frac{dP_{TM}}{dt} + K_{UF}*P_{TM} = Q_{UF}+Q_L \tag{1.5}$$

In the case of a constant ultrafiltration rate $Q_{UF}$ and a suddenly occurring leakage $Q_L$ at the time t=0, the following simple solution is obtained:

$$P_{TM}(t) = \frac{Q_{UF}}{K_{UF}} + \frac{Q_L}{K_{UF}}\left(1 - e^{\frac{t}{\tau}}\right) \text{ where} \tag{1.6}$$

$$\tau = \frac{C}{K_{UF}} \tag{1.7}$$

In a hard system (C=0.01 ml/mm Hg) and a high-flux dialyzer (e.g. F80 with $K_{UF}$=55 ml/Hg), the time constant is $\tau$=0.72 sec. In a low-flux dialyzer (e.g. $K_{UF}$=2 ml/h/mm Hg) and a soft system (C=0.05 ml/mm Hg) the time constant is $\tau$=90 sec.

After the new state of equilibrium $P_{TM}$ (t>5*$\tau$) is reached, the pressure $P_{TM}$ has changed by:

$$\Delta P_{TM} = P_{TM}(t > 5*\tau) - P_{TM}(0) = \frac{Q_L}{K_{UF}} \tag{1.8}$$

In a high-flux dialyzer (e.g. F80 with $K_{UF}$=55 ml/h/mm Hg), a leak rate of $Q_L$=125 ml/h generates a change of $\Delta P_{TM}$=+2.5 mm Hg and, in a low-flux dialyzer (e.g. $K_{UF}$=2 ml/h/mm Hg) it generates a change of $\Delta P_{TM}$=+62.5 mm Hg.

The following results can be derived from the above model.

The pressure changes to be expected are very small compared to the other pressures in the system. In the event of a sudden leak, the pressure changes over the course of a few seconds to minutes, whereas in the event of an insidious leak this delay may be ignored. According to equation (1.5), the UF rate $Q_{UF}$ and the leak rate $Q_L$ are equivalent interferences for the static pressure, so that the effect of a leak can be simulated by changing the UF rate.

Based on the change in the static pressure $\Delta P$, a leak rate $Q_L$ is calculated:

$$Q_L(t) = \frac{1}{E} * \Delta P(t) \tag{2.1}$$

where $$\Delta P(t) = P(t) - P(t-\Delta t) \tag{2.2}$$

where
P(t)=instantaneous pressure value;
P(t-$\Delta$t)=pressure reference value;
$\Delta$t=delay time of the reference value; and
E=sensitivity.

The sensitivity E depends on the used system components and is determined experimentally for each combination of dialyzers, hose sets and machine components. These values can be placed in the controlling and computing unit 20 and selected by the user.

It is also possible, at the start of a dialysis treatment, to generate a predetermined ultrafiltration flow $Q_{UF}$, to measure the pressure drop $\Delta P$ and to determine the sensitivity E with $Q_L$=$Q_{UF}$ with the aid of equation (2.1).

The delay time $\Delta$t is the time difference of the mean points of the averaging intervals. It should be greater than the mean value of the two averaging times $T_{P(t)}$ and $T_{P(t-\Delta t)}$ so that P(t) and P(t-$\Delta$t) independently of one another are:

$$\Delta t \geq (T_{P(t)} + T_{P(t-\Delta t)})/2 \tag{2.3}$$

To form the reference value P(t-$\Delta$t) there are two possibilities:
1. The reference value is adapted to the instantaneous pressure P(t) with the delay time $\Delta$t:

$$\Delta t = \text{constant} \tag{2.4a}$$

2. The initial reference value is maintained and only set to the instantaneous pressure valve sporadically, e.g. after a pressure-holding test:

$$\Delta t = t \text{ d.h. } P(t-\Delta t) = P(0) = \text{constant} \tag{2.4b}$$

On the basis of the statistical variations in the pressure signals, reliable detection of a leak is only possible if the leak rate exceeds the uncertainty range U. Using the Gaussian law of propagation of measurement uncertainties, equation (2.1) and equation (2.2) give:

$$U = k_{1-\alpha} * \frac{1}{E} * \sqrt{\sigma_{P(t)}^2 + \sigma_{P(t-\Delta t)}^2} \tag{2.5}$$

where $k_{1-\alpha}$ indicates the quantile of the normal distribution for a confidence level of 1-$\alpha$.

The standard deviation diminishes as the averaging time T increases:

$$\frac{\sigma(T_2)}{\sigma(T_1)} = \sqrt{\frac{T_1}{T_2}} \tag{2.6}$$

The averaging time of the reference value P(t-$\Delta$t) should be circa ten times as great as that of the instantaneous pressure P(t). This part can be ignored and the uncertainty reduces to:

$$U = k_{1-\alpha} * \frac{\sigma_{P(t)}}{E} \tag{2.7}$$

Since the leak rates with $Q_L$<U cannot be reliably detected, it is necessary to carry out a cyclic pressure-holding test with the period $T_{zyk.P}$:

$$T_{zyk.P} = \frac{500 \text{ ml}}{U} \tag{2.8}$$

If the period $T_{zyk.P}$ is greater than the duration of treatment, the cyclic pressure-holding test can be dispensed with. This can be achieved, within certain limits, by prolongation of the averaging times $T_{P(t)}$ and $T_{P(t-\Delta t)}$.

If a certain threshold value is exceeded, this need not be reacted to immediately, and instead it is possible to wait for a certain time to see whether the state stabilizes or whether it was only an artifact. With regard to patient safety, the leakage volume $V_L$ is decisive and can be represented as follows:

$$V_L(t) = \int_{t-\Delta t}^{t} Q_L(t')dt' = \frac{1}{E}\int_{t-\Delta t}^{t} \Delta P(t')dt' \tag{2.9}$$

The functioning of the device according to the invention for detecting a leakage is now described in greater detail.

Before the blood treatment, the integrity of the fluid system is checked using the means 25 and in accordance with the method described in German Patent Application No. 42 39 937 A1. If the system is integral, the blood treatment is initiated. During the blood treatment, the pressure upstream ($P_{D1}$) and downstream ($P_{D2}$) is measured with the pressure sensors 33 and 41. From the pressure upstream and downstream of the dialysis fluid chamber, the means 37 of the controlling and computing unit calculate the linear combination $P_{DM}=(P_{D1}+P_{D2})/2$, which is very strongly influenced by a leakage.

Figure 2:
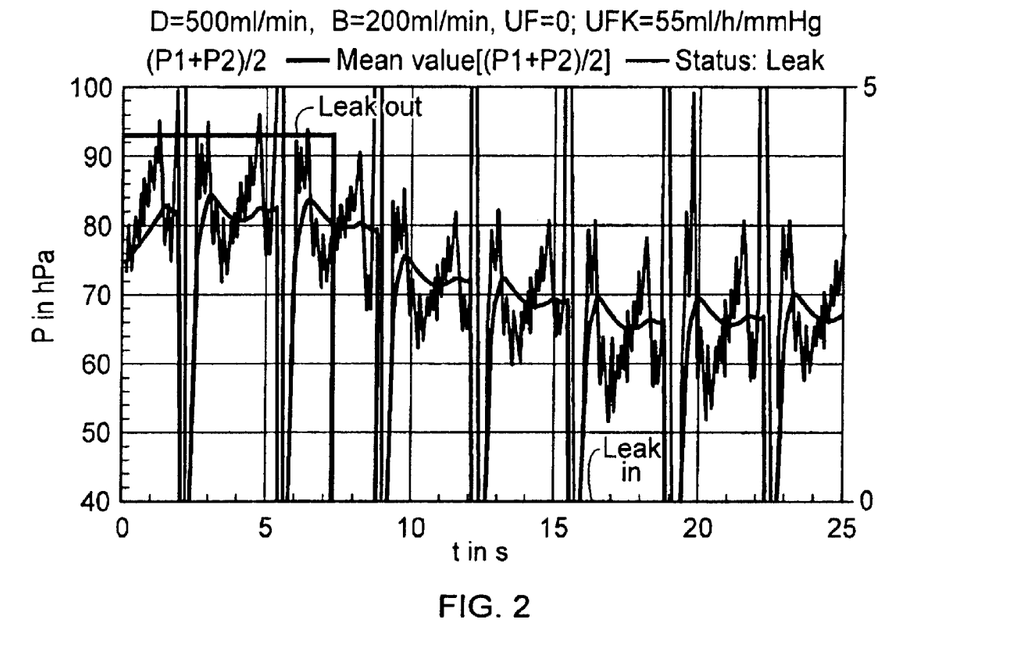
FIG. 2 shows the time course of the recorded pressure value.

FIG. 2 shows the time course of $P_{DM}$ and its mean value during a balance chamber cycle before and after the occurrence of a leak, assuming a dialysis fluid flow of 500 ml/min, a blood flow of 200 ml/min and an ultrafiltration rate UF=0. The ultrafiltration coefficient UFK is 55 ml/h/mm Hg.

Figure 3:
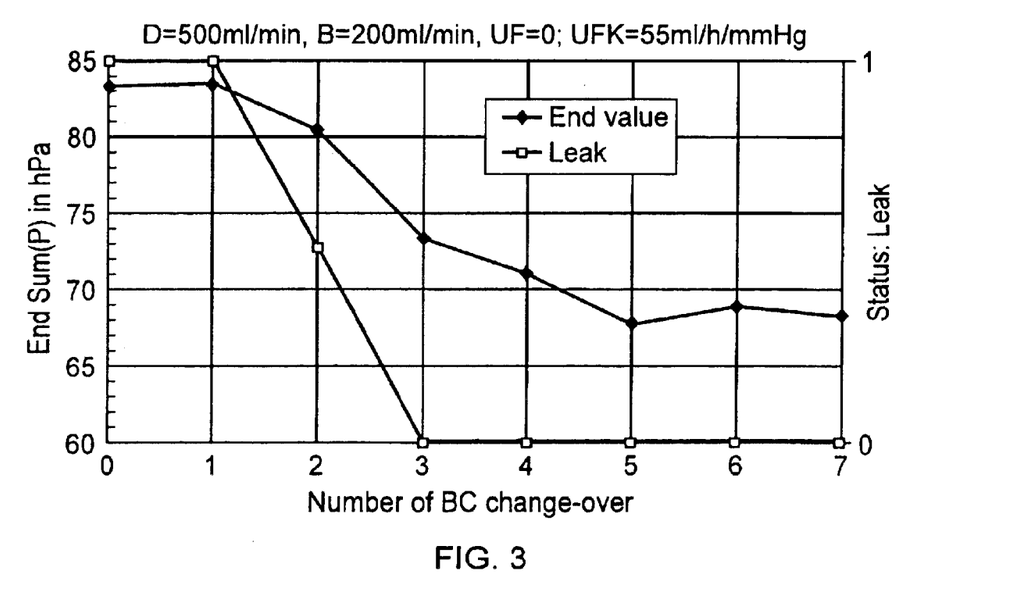
FIG. 3 shows the time course of the recorded mean value of the pressure value.

FIG. 3 shows the mean value of $P_{DM}$ between two balance chamber change-overs before and after the occurrence of the leak in the same dialysis fluid and blood flow. After each balance chamber change-over, a new mean value is once again formed. The mean value is in each case the end value of the averaging before the next balance chamber change-over. The decrease in pressure can be clearly detected after the occurrence of the leakage. However, the averaging interval can also include a plurality of balance chamber cycles in order to obtain a sufficient smoothing, especially in the case of high dialysis fluid flows and consequently small averaging intervals.

The measurement of the pressure $P_{DM}$ takes place during a predetermined period of the duration of treatment, i.e. until the time at which a possible leak is detected. Within the predetermined period of the duration of treatment, the leak rates are calculated at predetermined time intervals, which can again include a plurality of balance chamber cycles, via the means 38, by determining the value of the difference between the mean value of the pressure $P_{DM}$ in a subsequent cycle, which can include a plurality of balance chamber cycles, and the mean value of the pressure in a preceding cycle. During the blood treatment, the leakage volume in the predetermined period is calculated according to equation (2.9) from the individual leak rates in the predetermined time intervals by summation (integration). The calculation of the leakage volume is done by the means 39 of the controlling and computing unit 20. The means 40 of the controlling and computing unit 20 compare the leakage volume with a predetermined limit value, for example, 400 ml.

If the leakage volume is above the limit value, this is an indication of a possible loss of leaktightness in the fluid system. In this case, an alarm can be given immediately by the alarm means 35. However, the possible loss of leaktightness of the system is preferably verified by the means 25 which carries out the conventional pressure-holding test. For this purpose, the controlling and computing unit 20 interrupts the blood treatment and the means 25 separates the dialyzer from the dialysis fluid system by the shut-off members 28, 29 being closed and the bypass valve 27 being opened. Only when the means 25 detects a loss of leaktightness in the fluid system, the alarm means 35 emits an alarm. Otherwise, the treatment is continued again, the fluid system being continuously checked for possible loss of leaktightness with the device according to the invention. Should the device again detect a leakage, the blood treatment is again interrupted in order once again to verify the loss of leaktightness via the means 25.

With the method and device described above, it is possible in particular to detect suddenly occurring leaks without, in principle, necessitating an interruption of the treatment. By contrast, in order to detect insidious leaks it has proven advantageous to use, as a pressure reference value, not the pressure in the preceding cycle, but instead the initial pressure value measured at the start of the treatment.

In an alternative embodiment of the device and method according to the invention, it is not the pressure $P_{DM}$ that is measured, but instead the transmembrane pressure. The available pressure sensors are used to determine the transmembrane pressure TMP2, which is calculated from the difference of the pressure $P_{B2}$ downstream of the blood chamber 3 of the dialyzer 1 and the pressure $P_{DM}$, where the pressure $P_{B2}$ is measured with the pressure sensor 42. Otherwise, this embodiment does not differ from the initially described device. Alternatively, it is also possible for only the pressure $P_{B2}$ to be measured, in which case the measurement values are assessed as in the aforementioned methods.

Figure 4:
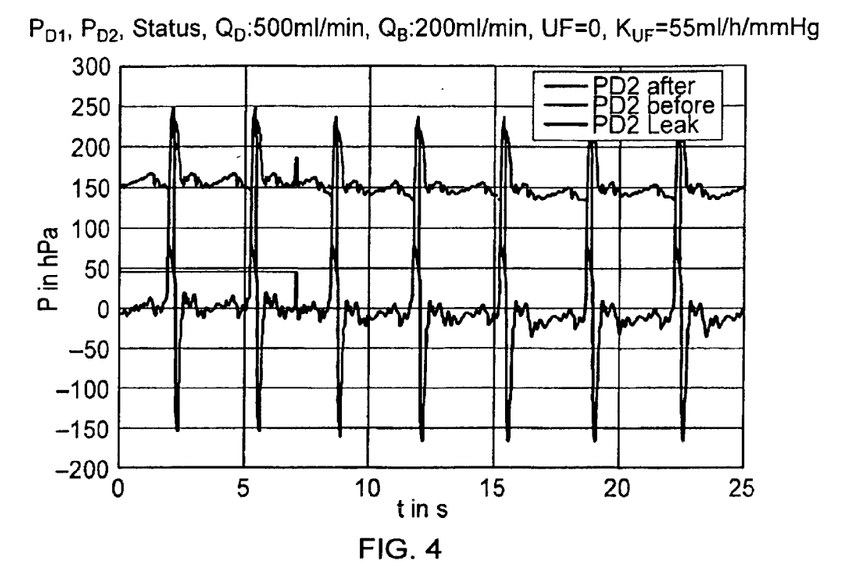
FIG. 4 shows the pressure course of $P_{D1}$ and $P_{D2}$ over time.

The pressure values measured with the sensors are superposed by interference variables. FIG. 4 shows the pressure $P_{D1}$ and $P_{D2}$ as a function of time, superposed by the periodic interference variables. The time signal of the pressures $P_{D1}$ and $P_{D2}$ is dominated by the positive and negative pressure peaks at the changeover of the balance chamber means 14. The smaller pressure variations are generated by the blood pump 6. On each stroke of the balance chamber 13, the ultrafiltration pump 19 generates a negative pressure peak.

The means 37 for detecting the pressure measurement values eliminate the known interference variables before the mean is formed. The known interference sources have the following effects on the measured pressure values.

The blood pump 6 generates the static pressure in the system. The constant pressure component is superposed by a signal which can be attributed to the effect of the rotors and the onward transportation of the blood. The maximum of the signal on the blood side is typically 50 hPa and on the dialysate side circa 10 hPa ($Q_b$=300 ml/min). The period duration is of the order of magnitude of 1 second. The pressure values downstream of the blood chamber 3 of the dialyzer 1 are subject to less interference than the pressure values upstream of the blood chamber. Measurement of the pressure $P_{B2}$ is therefore advantageous. Since the mean static pressure in the system also changes with the blood volume rate, the leakage monitoring after a change in the blood volume rate is preferably discontinued until the new stationary state is reached.

Figure 5:
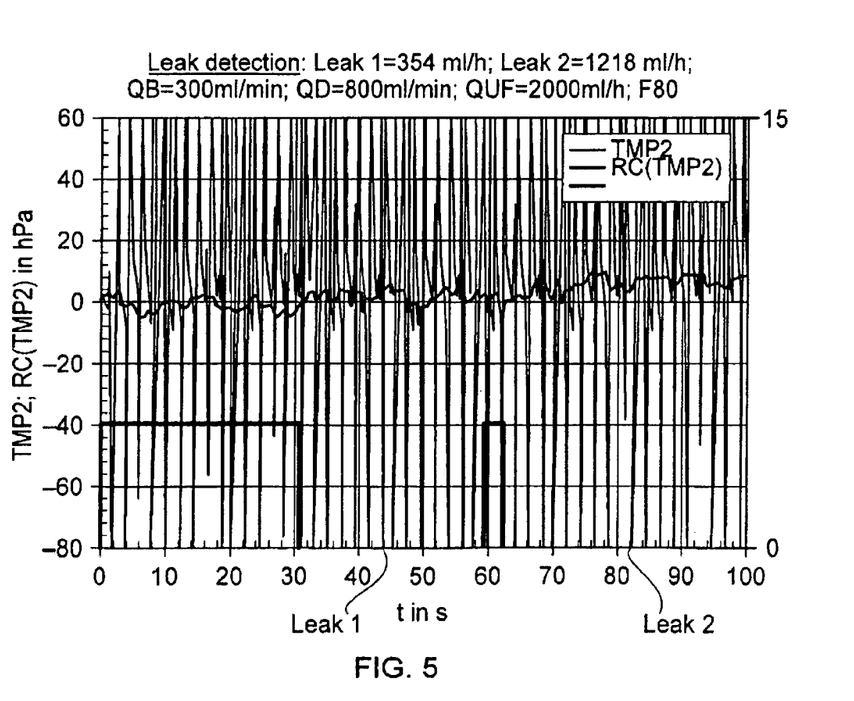
FIG. 5 shows the time course of the transmembrane pressure and of the corrected transmembrane pressure TMP2.
Figure 6:
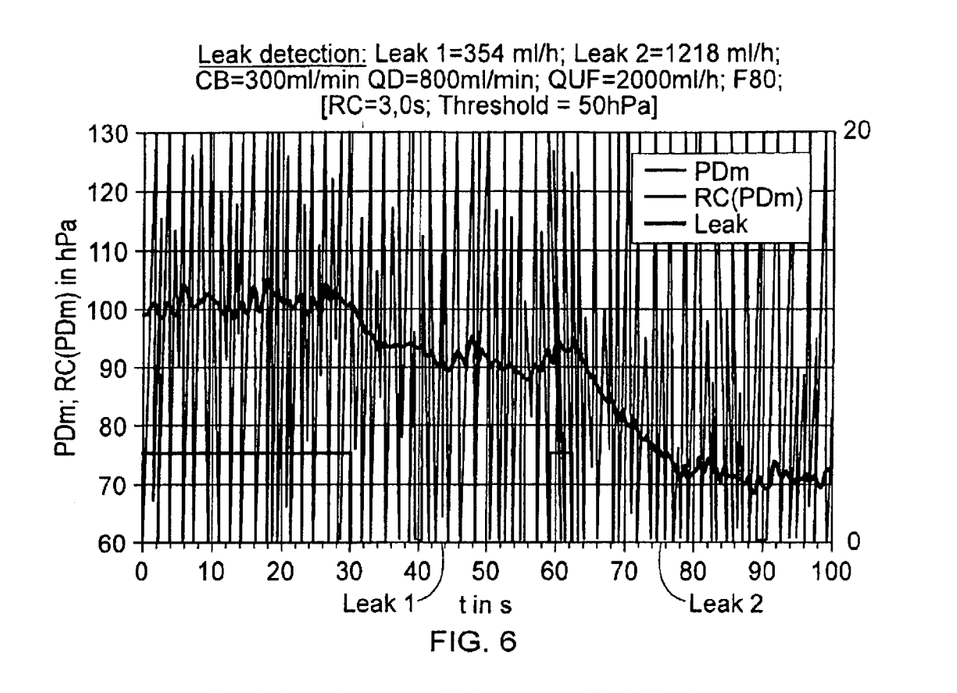
FIG. 6 shows the time course of the pressure $P_{Dm}$ and of the corrected pressure $P_{Dm}$.
Figure 7:
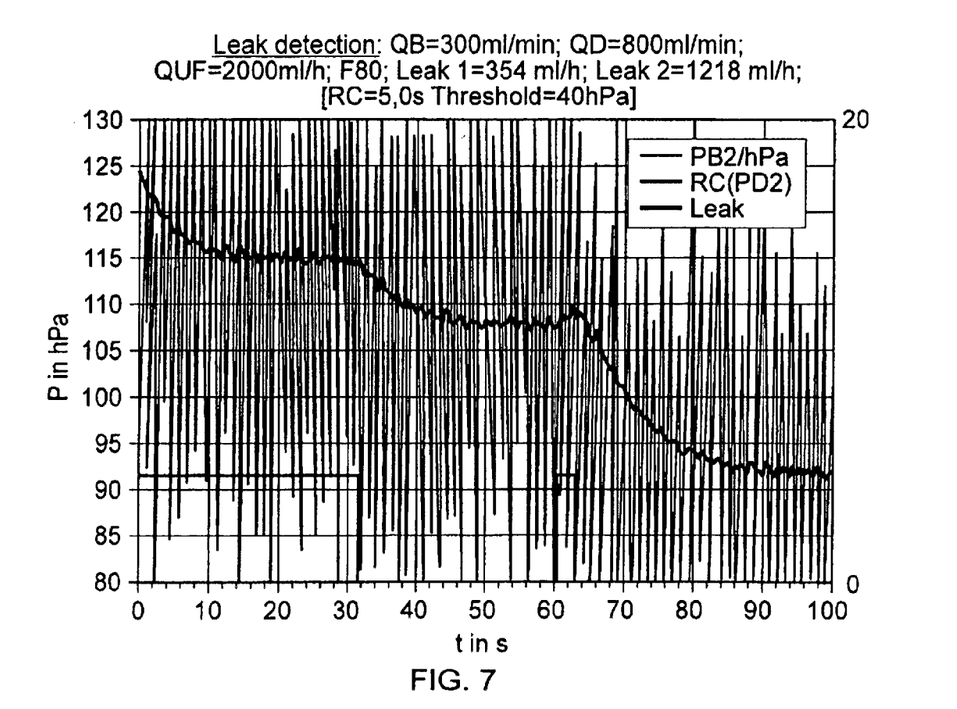
FIG. 7 shows the time course of the pressure $P_{B2}$ and of the corrected pressure $P_{B2}$.

In the following laboratory test, the signals were smoothed using a digital lowpass filter. FIGS. 5, 6 and 7 show the unsmoothed signals TMP2, $P_{DM}$ and $P_{B2}$ and the filtered signals RC(TMP2), RC($P_{DM}$) and RC($P_{B2}$) for two different leak rates.

The results are presented in the following tables (Tables 4.1, 4.2 and 4.3). The column "StdDev" contains the empirical standard deviation $\sigma_{p(t)}$ and the column "U" the uncertainty range according to equation (2.7). In the tables, the confidence level, 1−α=95%, and thus $k_{1-\alpha}$=2 were used.

The uncertainty U represents the minimum leak rate which differs significantly from the statistical variations of the measurement parameters.

TABLE 4.1

Results of the $P_{TM2}$ measurement

|  | $Q_L$ [ml/hl] | $\Delta P_{TM}$ [hPa] | $1/E_{PTM2}$ [ml/h/hPa] | StdDev[hPa] | U [ml/h] |
|---|---|---|---|---|---|
| Leak 1 | 354 | +3.1 | +114 | 2.1 | 491 |
| Leak 2 | 1218 | +7.8 | +156 | 2.1 | 669 |

TABLE 4.2

Results of the $P_{Dm}$ measurement

| | $Q_L$ [ml/h] | $\Delta P_{Dm}$ [hPa] | $1/E_{PDm}$ [ml/h/hPa] | StdDev[hPa] | U [ml/h] |
|---|---|---|---|---|---|
| Leak 1 | 354 | −10.7 | −33.1 | 1.6 | 107 |
| Leak 2 | 1218 | −30.3 | −40.2 | 1.6 | 129 |

TABLE 4.3

Results of the $P_{B2}$ measurement

| | $Q_L$ [ml/h] | $\Delta P_{B2}$ [hPa] | $1/E_{PB2}$ [ml/h/hPa] | StdDev[hPa] | U [ml/h] |
|---|---|---|---|---|---|
| Leak 1 | 354 | −7.1 | −49.6 | 0.48 | 47 |
| Leak 2 | 1218 | −23.0 | −52.9 | 0.48 | 50 |

In this laboratory test, the pressure signals $P_{Dm}$ and $P_{B2}$ have the statistical accuracy for monitoring the maximum leak rate of 125 ml/h.

What is claimed is:

1. A method for detecting a leakage in a fluid system of a blood treatment apparatus having an extracorporeal blood circuit, said method comprising:
    continuously measuring a pressure in the fluid system during a predetermined period of the duration of the blood treatment;
    calculating leak rates from changes in the pressure at predetermined time intervals of the predetermined period of the duration of the blood treatment;
    calculating a leakage volume in the predetermined period of the duration of the blood treatment from the leak rates; and
    comparing the leakage volume to a predetermined limit value.

2. The method according to claim 1, further comprising:
    calculating the changes in the pressure at predetermined time intervals by comparing the pressure in the fluid system to a pressure reference value.

3. The method according to claim 2, wherein the pressure reference value is equal to a pressure value in the fluid system which was measured during a preceding predetermined period of the duration of the blood treatment.

4. The method according to claim 2, wherein the pressure reference value is constant.

5. The method according to claim 2, wherein the pressure reference value is a mean value of a plurality of pressure values measured in an averaging interval.

6. The method according to claim 1, further comprising:
    generating an alarm if the leakage volume exceeds the predetermined limit value.

7. The method according to claim 1, further comprising:
    if the leakage volume exceeds the predetermined limit value, interrupting the blood treatment and conducting a pressure-holding test in the fluid system in order to check said fluid system for a loss of leaktightness.

8. The method according to claim 7, further comprising:
    generating an alarm if the pressure-holding test indicates the loss of leaktightness.

9. The method according to claim 1, wherein the blood treatment apparatus includes a dialyzer which is divided by a semipermeable membrane into a blood chamber and a dialysis fluid chamber, wherein blood flows into the blood chamber via a blood delivery line and flows out of the blood chamber via a blood discharge line, and dialysis fluid flows into the dialysis fluid chamber via a dialysis fluid delivery line and flows out of the dialysis fluid chamber via a dialysis fluid discharge line.

10. The method according to claim 9, wherein the pressure in the fluid system is continuously measured in at least one of the dialysis fluid delivery line upstream of the dialyzer, the dialysis fluid discharge line downstream of the dialyzer, and the blood discharge line downstream of the blood chamber.

11. A device for detecting a leakage in a fluid system of a blood treatment apparatus having an extracorporeal blood circuit, the device comprising:
    a controlling and computing unit, the controlling and computing unit comprising:
        a means for continuously measuring a pressure in the fluid system during a predetermined period of the duration of the blood treatment;
        a means for calculating leak rates from changes in the pressure at predetermined time intervals of the predetermined period of the duration of the blood treatment;
        a means for calculating a leakage volume in the predetermined period of the duration of the blood treatment from the leak rates; and
        a means for comparing the leakage volume to a predetermined limit value.

12. The device according to claim 11, wherein the means for calculating leak rates are designed to calculate the changes in the pressure by comparing the pressure in the fluid system to a pressure reference value.

13. The device according to claim 12, wherein the pressure reference value is equal to a pressure value in the fluid system which was measured during a preceding predetermined period of the duration of the blood treatment.

14. The device according to claim 12, wherein the pressure reference value is constant.

15. The device according to claim 12, wherein the pressure reference value is a mean value of a plurality of pressure values measured in an averaging interval.

16. The device according to claim 11, further comprising:
    an alarm device which generates an alarm if the leakage volume exceeds the predetermined limit value.

17. The device according to claim 11, further comprising:
    a means for checking the fluid system for a loss of leaktightness via a pressure-holding test in the fluid system, wherein the controlling and computing unit is designed to interrupt the blood treatment, and the means for checking the fluid system for a loss of leaktightness via a pressure-holding test can be activated to check the fluid system for a loss of leaktightness if the leakage volume exceeds the predetermined limit value.

18. The device according to claim 17, further comprising:
    an alarm device which generates an alarm if the pressure-holding test indicates the loss of leaktightness.

19. The device according to claim 11, wherein the blood treatment apparatus includes:
    a dialyzer which is divided by a semipermeable membrane into a blood chamber and a dialysis fluid chamber;
    a blood delivery line connected to the blood chamber for delivering blood into the blood chamber;

a blood discharge line connected to the blood chamber for removing blood from the blood chamber;

a dialysis fluid delivery line connected to the dialysis fluid chamber for delivering dialysis fluid into the dialysis fluid chamber; and a dialysis fluid discharge line connected to the dialysis fluid chamber for removing dialysis fluid from the dialysis fluid chamber.

20. The device according to claim 19, wherein the means for continuously measuring a pressure in the fluid system includes a pressure sensor measuring the pressure in at least one of the dialysis fluid delivery line upstream of the dialyzer, the dialysis fluid discharge line downstream of the dialyzer, and the blood discharge line downstream of the dialyzer.

* * * * *

(12) EX PARTE REEXAMINATION CERTIFICATE (6818th)

United States Patent
Balschat et al.

(10) Number: US 6,804,991 C1
(45) Certificate Issued: May 12, 2009

(54) METHOD AND DEVICE FOR DETECTING A LEAKAGE IN A FLUID SYSTEM OF A BLOOD TREATMENT APPARATUS

(75) Inventors: Klaus Balschat, Schwebheim (DE); Helmuth Ender, Zeil am Main (DE); Alfred Gagel, Litzendorf (DE); Reiner Spickermann, Wasserlosen-Burghausen (DE)

(73) Assignee: Fresenius Medical Care Deutschland GmbH, Bad Homburg (DE)

Reexamination Request:
No. 90/008,870, Nov. 1, 2007

Reexamination Certificate for:
Patent No.: 6,804,991
Issued: Oct. 19, 2004
Appl. No.: 10/342,851
Filed: Jan. 14, 2003

(30) Foreign Application Priority Data

Jan. 15, 2002 (DE) .......................... 102 01 109

(51) Int. Cl.
*G01M 3/04* (2006.01)

(52) U.S. Cl. .................. 73/40.5 R; 73/1.35; 210/90; 210/646; 604/4.01

(58) Field of Classification Search ................ 73/40.5 R
See application file for complete search history.

(56) References Cited

U.S. PATENT DOCUMENTS

| 5,580,460 | A  | 12/1996 | Polaschegg | .................. 210/646 |
| 5,674,404 | A  | 10/1997 | Kenley | ........................ 210/741 |
| 6,481,265 | B1 | 11/2002 | Weber | ............................ 73/40 |

OTHER PUBLICATIONS

Merle C. Potter and David C. Wiggert with Midhat Hondzo, Mechanics of Fluids Second Edition, 1997, pp. 645–651, Prentice Hall, Upper Saddle River, NJ.

*Primary Examiner*—Pia Tibbits (57) ABSTRACT

In order to detect a leakage in a fluid system of a blood treatment apparatus having an extracorporeal blood circuit, the pressure in the fluid system is measured continuously during a predetermined period of the duration of treatment, and the leak rates are calculated from the change in the pressure at predetermined time intervals of the predetermined period of the duration of treatment. The leakage volume in the predetermined period of the duration of treatment is calculated from the leak rates, and the leakage volume is compared with a predetermined limit value. If the leakage volume is greater than the limit value, this indicates a possible loss of leaktightness in the system. This can be verified with a conventional pressure-holding test. The method and device are characterized by the fact that it is not necessary in principle to interrupt the blood treatment in order to detect a loss of leaktightness.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–20 is confirmed.

New claims 21–54 are added and determined to be patentable.

21. *The method of claim 3, wherein the leak rate $Q_L$ at time t is expressed by the equation*

$$Q_L(t) = \frac{1}{E}\Delta P(t)$$

*wherein*

$$\Delta P(t) = P(t) - P(t-\Delta t)$$

*and wherein*
  *$P(t)$=the instantaneous pressure value,*
  *$P(t-\Delta t)$=the pressure reference value,*
  *$\Delta t$=the delay time of the reference value, and*
  *$E$=the sensitivity of the fluid system.*

22. *The method of claim 21, wherein the leakage volume $V_L$ is expressed by the equation*

$$V_L = \int_{t-\Delta t}^{t} Q_L(t')dt'.$$

23. *The method according to claim 22, further comprising: generating an alarm if the leakage volume exceeds the predetermined limit value.*

24. *The method according to claim 22, further comprising: if the leakage volume exceeds the predetermined limit value, interrupting the blood treatment and conducting a pressure-holding test in the fluid system in order to check said fluid system for a loss of leaktightness.*

25. *The method according to claim 24, further comprising: generating an alarm if the pressure-holding test indicates the loss of leaktightness.*

26. *The method according to claim 22, wherein the blood treatment apparatus includes a dialyzer which is divided by a semipermeable membrane into a blood chamber and a dialysis fluid chamber, wherein blood flows into the blood chamber via a blood delivery line and flows out of the blood chamber via a blood discharge line, and dialysis fluid flows into the dialysis fluid chamber via a dialysis fluid delivery line and flows out of the dialysis fluid chamber via a dialysis fluid discharge line.*

27. *The method according to claim 26, wherein the pressure in the fluid system is continuously measured in at least one of the dialysis fluid delivery line upstream of the dialyzer, the dialysis fluid discharge line downstream of the dialyzer, and the blood discharge line downstream of the blood chamber.*

28. *The device of claim 13, wherein the leak rate $Q_L$ at time t is calculated according to the equation*

$$Q_L(t) = \frac{1}{E}\Delta P(t)$$

*wherein*

$$\Delta P(t) = P(t) - P(t-\Delta t)$$

*and wherein*
  *$P(t)$=the instantaneous pressure value,*
  *$P(t-\Delta t)$=the pressure reference value,*
  *$\Delta t$=delay time of the reference value, and*
  *$E$=the sensitivity of the fluid system.*

29. *The device of claim 28, wherein the leakage volume $V_L$ is calculated according to the equation*

$$V_L = \int_{t-\Delta t}^{t} Q_L(t')dt'.$$

30. *The device according to claim 29, further comprising: an alarm device which generates an alarm if the leakage volume exceeds the predetermined limit value.*

31. *The device according to claim 29, further comprising: a means for checking the fluid system for a loss of leaktightness via a pressure-holding test in the fluid system, wherein the controlling and computing unit is designed to interrupt the blood treatment, and the means for checking the fluid system for a loss of leaktightness via a pressure-holding test can be activated to check the fluid system for a loss of leaktightness if the leakage volume exceeds the predetermined limit value.*

32. *The device according to claim 31, further comprising: an alarm device which generates an alarm if the pressure-holding test indicates a loss of leaktightness.*

33. *The device according to claim 29, wherein the blood treatment apparatus includes a dialyzer which is divided by a semipermeable membrane into a blood chamber and a dialysis fluid chamber, wherein blood flows into the blood chamber via a blood delivery line and flows out of the blood chamber via a blood discharge line, and dialysis fluid flows into the dialysis fluid chamber via a dialysis fluid delivery line and flows out of the dialysis fluid chamber via a dialysis fluid discharge line.*

34. *The device according to claim 33, wherein the pressure in the fluid system is continously measured in at least one of the dialysis fluid delivery line upstream of the dialyzer, the dialysis fluid discharge line downstream of the dialyzer, and the blood discharge line downstream of the blood chamber.*

35. *The method of claim 1, wherein the leakage volume is calculated by integration of the calculated leak rates.*

36. *The method according to claim 35, further comprising: calculating the changes in the pressure at predetermined time intervals by comparing the pressure in the fluid system to a pressure reference value.*

37. *The method according to claim 36, wherein the reference value is equal to a pressure value in the fluid system which was measured during a preceding predetermined period of the duration of the blood treatment.*

38. *The method according to claim 36, wherein the pressure reference value is constant.*

39. The method according to claim 36, wherein the pressure reference value is a mean value of a plurality of presure values measured in an averaging interval.

40. The method according to claim 35, further comprising: generating an alarm if the leakage volume exceeds the predetermined limit value.

41. The method according to claim 35, further comprising: if the leakage volume exceeds the predetermined limit value, interrupting the blood treatment and conducting a pressure-holding test in the fluid system in order to check said fluid system for a loss of leaktightness.

42. The method according to claim 41, further comprising: generating an alarm if the pressure-holding test indicates the loss of leaktightness.

43. The method according to claim 35, wherein the blood treatment apparatus includes a dialyzer which is divided by a semipermeable membrane into a blood chamber and a dialysis fluid chamber, wherein blood flows into the blood chamber via a blood delivery line and flows out of the blood chamber via a blood discharge line, and dialysis fluid flows into the dialysis fluid chamber via a dialysis fluid delivery line and flows out of the dialysis fluid chamber via a dialysis fluid discharge line.

44. The method according to claim 43, wherein the pressure in the fluid system is continuously measured in at least one of the dialysis fluid delivery line upstream of the dialyzer, the dialysis fluid discharge line downstream of the dialyzer, and the blood discharge line downstream of the blood chamber.

45. The device of claim 11, wherein the means for calculating leakage volume calculates leakage volume by integrating the calculated leak rates.

46. The device according to claim 45, wherein the means for calculating leak rates are designed to calculate the changes in the pressure by comparing the pressure in the fluid system to a pressure reference value.

47. The device according to claim 46, wherein the pressure reference value is equal to a pressure value in the fluid system which was measured during a preceding predetermined period of the duration of the blood treatment.

48. The device according to claim 46, wherein the pressure reference value is constant.

49. The device according to claim 46, wherein the pressure reference value is a mean value of a plurality of pressure values measured in an averaging interval.

50. The device according to claim 45, further comprising: an alarm device which generates an alarm if the leakage volume exceeds the predetermined limit value.

51. The device according to claim 45, further comprising: a means for checking the fluid system for a loss of leaktightness via a pressure-holding test in the fluid system, wherein the controlling and computing unit is designed to interrupt the blood treatment, and the means for checking the fluid system for a loss of leaktightness via a pressure-holding test can be activiated to check the fluid system for a loss of leaktightness if the leakage volume exceeds the predetermined limit value.

52. The device according to claim 51, further comprising: an alarm device which generates an alarm if the pressure-holding test indicates the loss of leaktightness.

53. The device according to claim 45, wherein the blood treatment apparatus includes: a dialyzer which is divided by a semipermeable membrane into a blood chamber and a dialysis fluid chamber; a blood delivery line connected to the blood chamber for delivering blood into the blood chamber; a blood discharge line connected to the blood chamber for removing blood from the blood chamber; a dialysis fluid delivery line connected to the dialysis fluid chamber for delivering dialysis fluid into the dialysis fluid chamber; and a dialysis fluid discharge line connected to the dialysis fluid chamber for removing dialysis fluid from the dialysis fluid chamber.

54. The device according to claim 53, wherein the means for continuously measuring a pressure in the fluid system includes a pressure sensor measuring the pressure in at least one of the dialysis fluid delivery line upstream of the dialyzer, the dialysis fluid discharge line downstream of the dialyzer, and the blood discharge line downstream of the blood chamber.

\* \* \* \* \*